United States Patent
Jin et al.

(10) Patent No.: US 10,213,172 B2
(45) Date of Patent: Feb. 26, 2019

(54) IMAGING METHOD AND SYSTEM OF TUBE VOLTAGE AND CURRENT OPTIMIZATION

(71) Applicant: GENERAL ELECTRIC COMPANY, Schenectady, NY (US)

(72) Inventors: Yannan Jin, Niskayuna, NY (US); Bruno Kristiaan Bernard De Man, Clifton Park, NY (US); Peter Michael Edic, Albany, NY (US); Paul Francis Fitzgerald, Schenectady, NY (US); Xue Rui, Clifton Park, NY (US); Yangyang Yao, Shanghai (CN); Zhye Yin, Schenectady, NY (US); Uwe Wiedmann, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 194 days.

(21) Appl. No.: 15/044,787

(22) Filed: Feb. 16, 2016

(65) Prior Publication Data
US 2016/0242712 A1 Aug. 25, 2016

Related U.S. Application Data

(60) Provisional application No. 62/118,660, filed on Feb. 20, 2015.

(51) Int. Cl.
*A61B 6/00* (2006.01)
*A61B 6/03* (2006.01)

(52) U.S. Cl.
CPC .............. *A61B 6/405* (2013.01); *A61B 6/032* (2013.01); *A61B 6/488* (2013.01); *A61B 6/5205* (2013.01); *A61B 6/542* (2013.01); *A61B 6/4233* (2013.01)

(58) Field of Classification Search
CPC ........ A61B 6/4233; A61B 6/542; A61B 6/545
(Continued)

(56) References Cited

U.S. PATENT DOCUMENTS 6,973,158 B2 12/2005 Besson
7,587,023 B2 9/2009 Hur
(Continued)

FOREIGN PATENT DOCUMENTS

EP 1512375 A1 3/2005
WO 2013103790 A1 7/2013

OTHER PUBLICATIONS

Hsieh et al., "Dual-energy X-ray CT with Fast-kVp Switch", GE Healthcare, 51st AAPM Annual Meeting, pp. 1-5, Mar. 4, 2014.
(Continued)

*Primary Examiner* — Don Wong
(74) *Attorney, Agent, or Firm* — GE Global Patent Operation; Seema Katragadda

(57) ABSTRACT

An imaging method includes executing a low-dose preparatory scan to an object by applying tube voltages and tube currents in an x-ray source, and generating a first image of the object corresponding to the low-dose preparatory scan. The method further includes generating image quality estimates and dose estimates view by view at least based on the first image. The method includes optimizing the tube voltages and the tube currents to generate optimal profiles for the tube voltage and the tube current. At least one of the optimal profiles for the tube voltage and the tube current is generated based on the image quality estimates and the dose estimates. The method includes executing an acquisition scan by applying the tube voltages and the tube currents based on the optimal profiles and generating a second image of the object corresponding to the acquisition scan. An imaging system is also provided.

20 Claims, 8 Drawing Sheets

(58) Field of Classification Search
USPC .......................................... 378/97, 108, 109
See application file for complete search history.

(56) References Cited

U.S. PATENT DOCUMENTS

| | | | |
|---|---|---|---|
| 7,924,969 B2 | 4/2011 | Yamakawa et al. | |
| 8,031,831 B2 | 10/2011 | Zou | |
| 8,155,263 B2 | 4/2012 | Wu et al. | |
| 2007/0147579 A1 | 6/2007 | De Man et al. | |
| 2012/0089377 A1* | 4/2012 | Erhard .................. | A61B 6/032 703/1 |
| 2012/0155609 A1* | 6/2012 | Lemminger ........... | A61B 6/032 378/62 |
| 2014/0177784 A1 | 6/2014 | Yu et al. | |

OTHER PUBLICATIONS

Bae, "Radiation Dose", MDCT, Mar. 23, 2015.

Yu et al., "Automatic selection of tube potential for radiation dose reduction in CT: a general strategy", Med Phys., vol. 37, Issue 1, pp. 234-243, Jan. 2010.

Sperl et al., "Computer-assisted scan protocol and reconstruction (CASPAR)-reduction of image noise and patient dose", Medical Imaging, IEEE Transactions on, vol. 29, Issue 3, pp. 724-732, Mar. 2010.

Li et al., "Simultaneous Reduction in Noise and Cross-Contamination Artifacts for Dual-Energy X-Ray CT", BioMed Research International, vol. 2013, pp. 1-8, 2013.

Tian et al., "Projection-based dose metric: accuracy testing and applications for CT design", Proc. SPIE 8668, Medical Imaging 2013: Physics of Medical Imaging, vol. 8668, Mar. 19, 2013.

Huh et al., "Fast kVp-switching dual energy CT for PET attenuation correction," 2009 IEEE Nuclear Science Symposium Conference Record (NSS/MIC), pp. 2510-2515, Oct. 24, 2009-Nov. 1, 2009.

International Search Report and Written Opinion issued in connection with corresponding Application No. PCT/US2016/018214 dated Jun. 1, 2016.

* cited by examiner

IMAGING METHOD AND SYSTEM OF TUBE VOLTAGE AND CURRENT OPTIMIZATION

CROSS REFERENCE TO RELATED APPLICATION

This patent application claims the benefit of priority, under 35 U.S.C. § 119, of U.S. Provisional Patent Application Ser. No. 62/118,660, filed Feb. 20, 2015, titled "IMAGING METHOD AND SYSTEM OF TUBE VOLTAGE AND CURRENT OPTIMIZATION" the entire disclosure of which is incorporated herein by reference.

BACKGROUND

Embodiments of the disclosure relate generally to an imaging method and an imaging system, and more particularly to an imaging method and an imaging system of tube voltage and current optimization for computed tomography (CT) scans.

X-ray scans and x-ray computed tomography (CT) scans are used in a wide range of medical and industrial settings to generate images of structures within a three-dimensional subject or object that are otherwise invisible to the naked eye. For example, CT scans of medical patients are used in a wide range of pathologies including, but not limited to, identification of tumors, infectious process, infarctions, calcification, hemorrhage, and trauma. In the description that follows, the disclosed methods apply equally to scanning one of a patient and object.

While x-ray and CT scans are widely used, the x-ray radiation that is generated during the scans may increase risk of cancer for the patient being scanned. One goal is to control the exposure to radiation for humans and other living subjects that undergo the CT scan while also generating images with sufficient clarity and resolution to be useful in diagnostic procedures. This balance between the need to use the lowest x-ray radiation possible while maintaining an image quality required for optimal identification of pathology is known as ALARA "as low as reasonably achievable." During a CT scan, an x-ray source, such as an x-ray emitting tube, rotates around the longitudinal axis of the patient while emitting x-ray radiation. Some of the x-ray energy passes through the patient to a detector on the opposite side of the patient from the x-ray emitter, while the patient absorbs a portion of the x-ray energy, known as the radiation dose. A lower-dose CT scan produces images that have a higher noise level and/or poor contrast-to-noise ratio, which can obscure detail about structures within the patient. Increasing the intensity of the x-ray exposure improves the quality of images, but the patient also absorbs additional x-ray radiation during the scan.

The amount of x-ray radiation delivered to the patient and the quality of the images are dependent on the energy fluence emitted from the x-ray source. When the x-ray tube is employed as a radiation source, the energy fluence is determined by the scanning parameters such as the tube current (mA) and the tube voltage (kV). The power output of the tube is expressed as a product of the tube current and the tube voltage. The dose that the patient receives from the CT scanner corresponds to the portion of the emitted power from the tube that is absorbed by the tissue in the body of the patient multiplied by the length of time that the patient is exposed to the x-rays from the tube. For example, higher levels of tube current and higher tube voltage generally result in a lower noise image, but deliver x-ray radiation to the patient at a correspondingly higher rate. In addition, the image quality and the dose can be different for different patients and/or applications when the power from the tube is the same. Currently, the same scan protocol and the same tube power are used to scan different patients.

It is desirable to provide a solution to address at least one of the above-mentioned problems.

BRIEF DESCRIPTION

An imaging method is provided. The method includes executing a low-dose preparatory scan to an object by applying tube voltages and tube currents to an x-ray source, and generating a first image of the object corresponding to the low-dose preparatory scan. The method further includes generating a number of image quality estimates and a number of dose estimates view by view at least based on the first image. The method further includes optimizing the tube voltages and the tube currents to generate optimal profiles for the tube voltages and the tube currents. At least one of the optimal profiles for the tube voltages and the tube currents is generated based on the image quality estimates and the dose estimates. The method further includes executing an acquisition scan by applying the tube voltages and the tube currents based on the optimal profiles and generating a second image of the object corresponding to the acquisition scan.

An imaging system is provided. The imaging system includes detectors, an x-ray source, and a controller. The x-ray source is configured to project x-rays towards the detectors. The controller is operatively connected to the x-ray source and the detectors, and configured to control the x-ray source and the detectors to execute a low dose preparatory scan to an object by applying tube voltages and tube currents to the x-ray source and generate a first image of the object corresponding to a low dose preparatory scan. The controller is further configured to generate a number of image quality estimates and a number of dose estimates view by view at least based on the first image. The controller is further configured to optimize the tube voltages and the tube currents to generate optimal profiles for the tube voltages and the tube currents. At least one of the optimal profiles for the tube voltages and the tube currents is generated based on the image quality estimates and the dose estimates. The controller is further configured to apply the x-ray source the tube voltages and the tube currents based on the optimal profiles to execute an acquisition scan and generate a second image of the object corresponding to the acquisition scan.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items, and terms such as "front", "back", "bottom", and/or "top", unless otherwise noted, are merely used for convenience of description, and are not limited to any one position or spatial orientation. Moreover, the terms "coupled" and "connected" are not intended to distinguish between a direct or indirect coupling/connection between two components. Rather, such components may be directly or indirectly coupled/connected unless otherwise indicated.

The operating environment of the present invention is described with respect to a four-slice computed tomography (CT) system for imaging of a multi-component object, such as a medical patient. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other types of radiation. The present invention will be described with respect to a "third-generation" CT scanner, but is equally applicable with other CT systems. For example, the invention is also applicable with systems having multiple source spots for increased flexibility in determining an optimal radiation profile by individually steering or activating the different sources.

Figure 1:
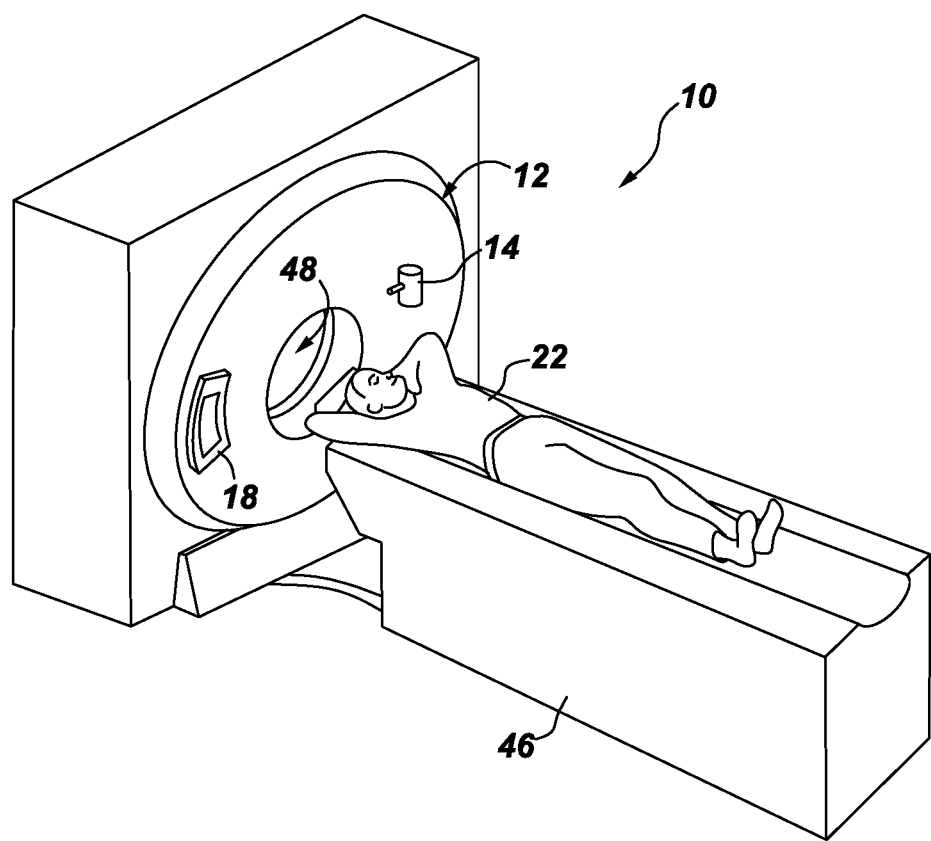
FIG. 1 is a perspective view of a CT imaging system according to one embodiment.
Figure 2:
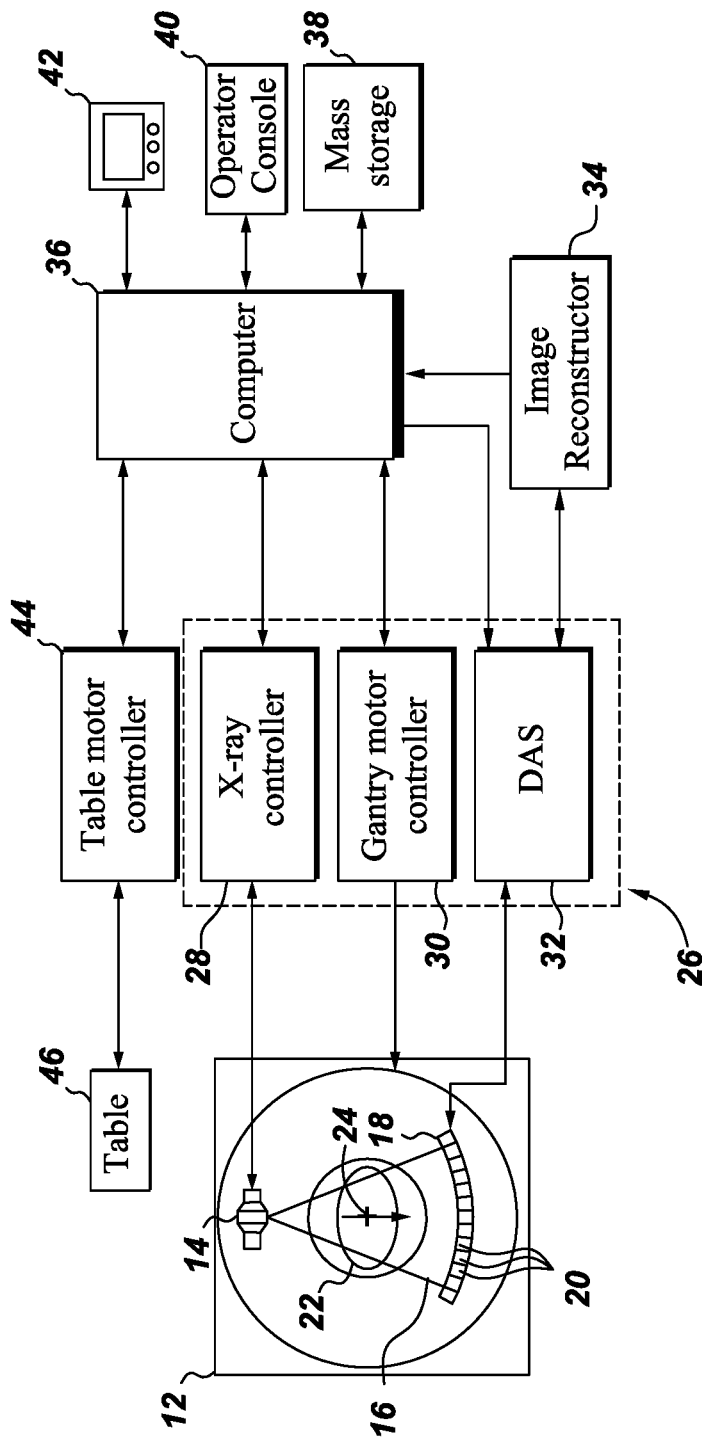
FIG. 2 is a schematic view of the CT imaging system in FIG. 1.

Referring to FIGS. 1 and 2, a CT imaging system 10 is shown as including a gantry 12 representative of a "third-generation" CT scanner. The gantry 12 has an x-ray source 14 that projects a beam of x-rays 16 toward a detector array 18 on the opposite side of the gantry 12. The detector array 18 includes multiple detectors 20 which together sense the transmitted x-rays that pass through a medical patient 22. Each detector 20 produces an electrical signal that represents the intensity of an impinging x-ray beam and hence the attenuated beam as it passes through the patient 22. During a scan to generate x-ray projection data, the gantry 12 and the components such as the x-ray source 14 and the detector array 18 mounted thereon rotate about a center of rotation 24. The x-ray source 14 and the detector array 18 on the gantry 12 may rotate 360 degrees about the center of rotation 24 to acquire data from the patient 22 at different view angles.

Rotation of the gantry 12 and the operation of the x-ray source 14 are governed by a control device 26 of the CT system 10. The control device 26 includes an x-ray controller 28 that provides power and timing signals to an x-ray source 14 and a gantry motor controller 30 that controls the rotational speed and position of the gantry 12. A data acquisition system (DAS) 32 in the control device 26 samples analog data from the detectors 20 and converts the data to digital signals for subsequent processing. An image reconstructor 34 receives sampled and digitized x-ray data from the DAS 32 and performs high speed reconstruction. The reconstructed image is applied as an input to a computer 36 which stores the image in a mass storage 38.

The computer 36 also receives commands and scanning parameters from an operator 40 that may have a keyboard. An associated display, such as a cathode ray tube display, 42 allows the operator 40 to observe the reconstructed image and other data from the computer 36. The commands and parameters supplied by the operator 40 are used by the computer 36 to provide control signals and information to the DAS 32, the x-ray controller 28 and the gantry motor controller 30. In addition, the computer 36 operates a table motor controller 44 which controls a motorized table 46 to position the patient 22 and the gantry 12. Particularly, the table 46 moves portions of the patient 22 through a gantry opening 48.

Embodiments of the present disclosure refer generally to an imaging method which is applicable for imaging an object such as a patient to achieve desired image quality with lowest radiation dose in CT. The present disclosure is directed to the imaging method to optimize peak tube voltages (kV) and tube currents (mA) on a view by view basis, using a low dose preparatory scan such as a scout scan along with dose reduction. The method includes executing the low-dose preparatory scan to the object and generating a first image of the object corresponding to the low-dose preparatory scan. The method further includes generating noise estimates and dose estimates on a view by view basis at least based on the first image and optimizing the tube voltage and the tube current to generate optimal profiles for the tube voltage and the tube current to be applied during scanning of the patient. In one embodiment, the noise estimates may include a volumetric map of noise variance. In another embodiment, the noise estimates may include an average noise variance for a region of interest. In one embodiment, the dose estimates may include a volumetric map of absorbed dose. In another embodiment, the dose estimates may include an average absorbed dose for a region of interest or an organ-weighted dose. At least one of the optimal profiles for the tube voltage and the tube current is optimized based on the noise estimates and the dose estimates. The method further includes executing an acquisition scan by applying the tube voltages and the tube currents based on the optimal profiles and generating a second image of the object corresponding to the acquisition scan.

The dependent parameters to be optimized are image quality and radiation dose; image quality is often defined with respect to the image noise. However, it will be appreciated by those skilled in the art that the present invention is equally applicable if image quality is defined with respect to image contrast, i.e. the contrast between two particular tissues of interest; or if image quality is defined in terms of a combination of contrast and noise, such as contrast-to-noise ratio; or if image quality is defined in terms that include contrast and/or noise and/or spatial resolution; or if image quality is defined in another matter related to the important parameters for the specific imaging task.

The profiles of tube voltage and the tube current are optimized based on the low-dose preparatory scan to the object to provide a personalized optimization protocol to reduce the radiation dose in a CT scan. The term "optimize"

in some embodiments may include the meaning of the terms "modulate" and "select", but not limited. The term "modulate" (or "modulation") herein means continuously changing the tube voltage and/or the tube current as the gantry rotates about the patient. The term "select" (or "selection") herein means choosing a constant value from a value group as the tube voltage or the tube current. The tube voltage may be modulated or selected and the tube current may also be modulated or selected. The tube voltage and the tube current profiles may be optimized sequentially or jointly. Some embodiments of the imaging method are detailed in sequential paragraphs along with figures.

Figure 3:
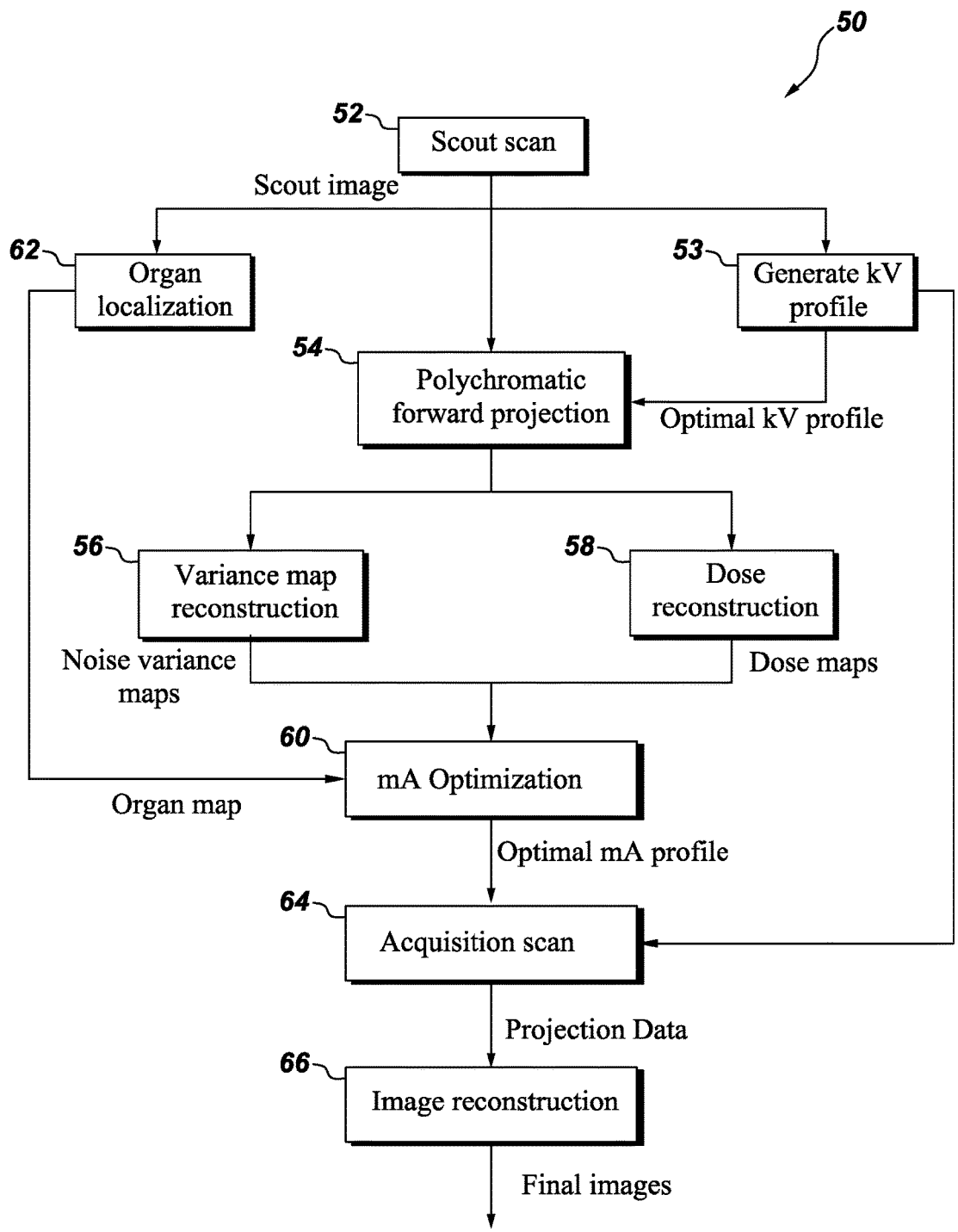
FIG. 3 is a flow chart of an imaging method according to one embodiment.

FIG. 3 illustrates a flow chart of a CT imaging method 50 according to one embodiment. In one embodiment, the CT imaging method 50 may be operated by the CT imaging system 10 in FIG. 1. The CT imaging method 50 includes executing a low-dose preparatory scan to an object in block 52. In one embodiment, the object is the patient 22 in FIGS. 1 and 2. The low-dose preparatory scan is a preparatory scan performed at low power to generate low-resolution images of the object. In this embodiment, the low-dose preparatory scan is a scout scan where low tube current is applied to the x-ray source 14 to scan the patient 22 and low radiation, for example about 0.05 mSv (millisievert) to 0.1 mSv, is absorbed. The scout scan may be a three-dimensional (3D) scout scan or a two-dimensional (2D) scout scan. A two-dimensional scout is well-known in the art; a three-dimensional scout scan includes acquisition of low-dose projection data suitable for reconstructing images corresponding to the 3D volumetric representation of the patient. In another embodiment, any other low dose preparatory scan may be employed to pre-scan the patient 22, including but not limited to a previous CT scan, MRI scan, or scan of the same patient from any other modality. In another embodiment, a virtual representation of the patient is employed as the preparatory scan, where the virtual representation of the patient is a selected patient model from a library of actual or simulated scans and adjusted to match the size of the actual patient; or the virtual representation of the patient is a composite of prior images of the patient from CT or other modalities combined with patient models, or the virtual representation of the patient is produced by some other means. A first image of the object is generated corresponding to the low dose preparatory scan. The first image is a preparatory image showing a rough structure within the object. The first image may be a reconstructed image or a projection image. In this embodiment, a scout image is generated based on projection data in the scout scan. In one embodiment, the scout image is smoothed and denoised to improve the quality of the image.

In the illustrated embodiment, in block 53, the tube voltage is optimized based on the first image for a constant tube current (or a normalized mA profile), such as 300 mA for each view, to generate the optimal voltage profile (kV profile) for the tube voltage. Details on generating the optimal voltage profile will be described in subsequent paragraphs.

The noise estimates and the dose estimates are generated view by view at least based on the first image. In this embodiment, the noise estimates and the dose estimates are generated based on the optimal voltage profile and the constant tube current. In this embodiment, the noise estimates are noise variance maps and the dose estimates are dose maps, but are not limited. For example, any map of an image quality metric may be suitable to use with the present method. In the illustrated embodiment, in block 54, projection data are generated based on the first image and the optimal voltage profile through forward projection of the image data using a polychromatic spectrum. And then the noise variance maps and the dose maps are generated view by view based on the projection data from the block 54, in blocks 56 and 58. The noise variance maps represent the noise contribution from each view. The noise variance maps may be utilized to represent the noise, signal-to-noise ratio, the square root of the noise, or something similar. The dose maps represent the dose contribution from each view. The dose maps may be utilized to represent the distribution of dose, dose weighted by organ sensitivity, a function of dose, or any other suitable metric.

In block 60, the tube currents are optimized view by view based on the noise variance maps and the dose maps to generate the optimal current profile (mA profile) for the tube current. In this embodiment, the tube current is modulated view by view. The tube current for a corresponding view is determined based on the noise variance map and the dose map for the corresponding view. In one embodiment, the tube current profile is optimized to make the noise lower than a desired noise threshold while minimizing the radiation dose. The dose is varied positive linearly with the tube current but the noise is varied inversely to the square root of tube current. In the illustrated embodiment, the method 50 further includes generating an organ map or localization of the object based on the first image in block 62. The organs of the patient are localized based on the scout image. For example, lungs, bones, soft tissue, heart and breasts can be localized in the organ map. In this embodiment, the tube current profile is optimized based on the organ map. The tube current is modulated to maintain the image quality in a certain region of interest (ROI) while minimizing the dose within the same ROI or in a different ROI. For example, the tube current is lowered for exposures where the x-ray source is proximal to a special organ, such as breasts which are quite sensitive to dose, to reduce the dose. The tube current may be increased for a specific organ, which may be required to reduce the noise so as to increase the image quality. In another embodiment, the tube current may be optimized according to particular applications.

In the illustrated embodiment, the tube voltage and the tube current profiles are optimized sequentially. The tube voltage profile is optimized first and then the tube current profile is optimized based on the tube voltage profile. In another embodiment, the tube current profile may be optimized first and then the tube voltage profile may be optimized based on the tube current profile.

In block 64, an acquisition scan is executed by applying the tube voltages and the tube currents based on the optimal profiles. The optimized tube voltage and the optimized tube current profiles are applied by the x-ray source to irradiate the object. Projection data corresponding to the acquisition scan are generated. In block 66, a second image of the object corresponding to the acquisition scan is generated. The second image is reconstructed based on the projection data from block 64. In one embodiment, the second image may be a final image displayed for diagnosis, treatment or the like.

Accordingly, the optimization of the tube current and the tube voltage profiles is patient and application dependent. The low-dose preparatory scan can be employed to generate the image of the individual patient and the tube current and the tube voltage profiles are optimized based on the image of the individual patient so as to achieve personalized protocol optimization. The optimization of the tube current and the tube voltage profiles can achieve the best image quality and dose tradeoff, for a specific patient size, patient anatomy, and clinical application.

Figure 4:
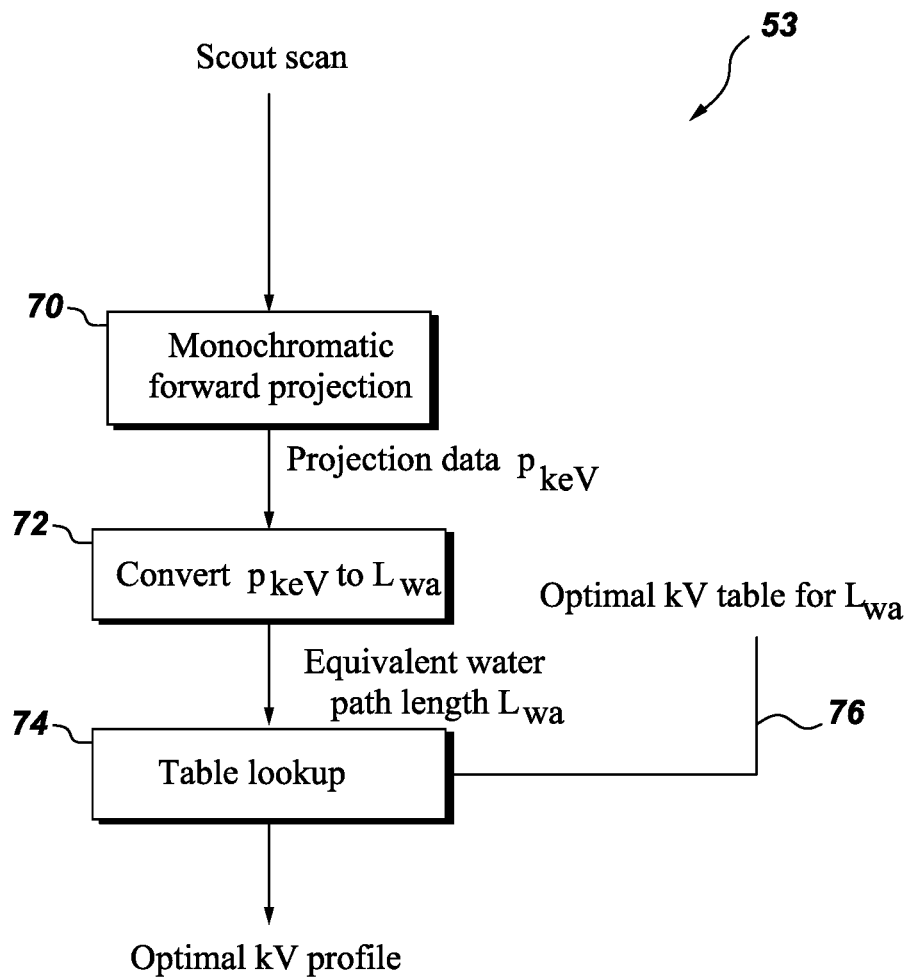
FIG. 4 is a flow chart of a step of the imaging method in FIG. 3 according to one embodiment.

FIG. 4 illustrates a flow chart of the process of generating the optimal voltage profile in the block 53 in FIG. 3 according to one embodiment. In block 70, projection data ($p_{keV}$) are generated based on the first image which is the scout image in this embodiment through forward projection of the image view by view basis using a monochromatic spectrum. A single spectrum (or energy) is chosen to generate the projection data. In one embodiment, the object is assumed to consist of water-equivalent materials, thus the optimal tube voltage profile is derived from a central ray passing through a given water path length. Accordingly, the spectrum including water attenuation is chosen, and the projection data using these data are generated.

In block 72, the projection data from the block 70 are converted to equivalent water path lengths ($L_{wa}$) in this embodiment. In block 74, the optimal voltage profile is generated based on the equivalent water path lengths through a lookup table 76 of the optimal tube voltage for each water path length to generate the optimal voltage profile.

Figure 5:
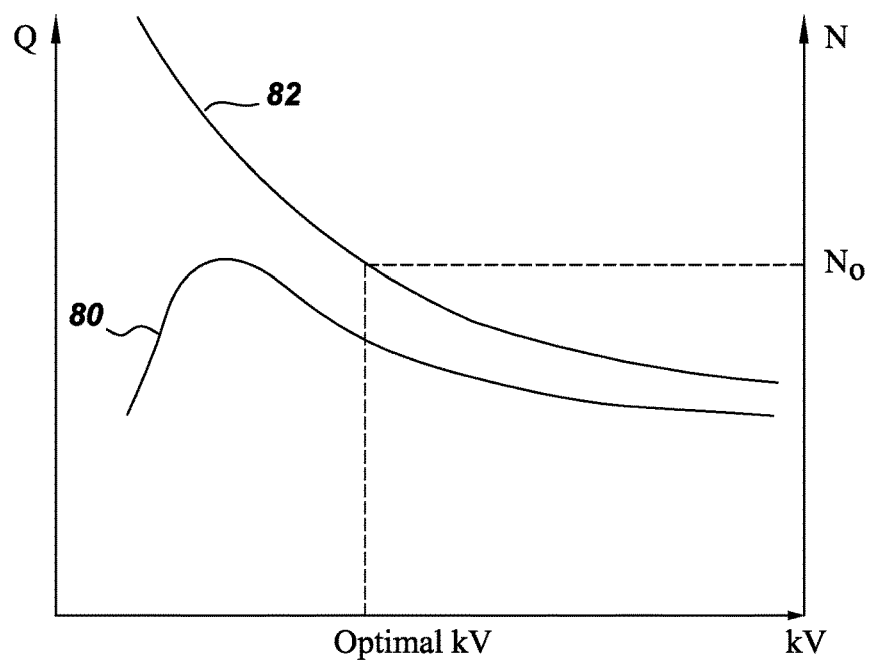
FIG. 5 is a waveform diagram of a waveform between Quality Factor and tube voltage and a waveform between noise and the tube voltage according to one embodiment.

FIG. 5 illustrates a waveform 80 between Quality Factor (Q-factor or Q) and the peak tube voltage (kV) and a waveform 82 between the noise (N) and the tube voltage kV for one water path length. The Q-factor is a factor of image quality which can be defined in various ways, for example as $CNR^2/D$ (i.e. $Q=CNR^2/D$), where CNR is contrast-to-noise ratio and D is radiation dose. The contrast is determined based on clinical applications and patient anatomy. For example, for coronary angiography the contrast could be defined as the attenuation difference between a contrast-enhancing material (often iodine but could be any contrast-enhancing material) and water; for a routine chest scan, the contrast could be defined as the attenuation difference between soft tissue and water. The Q-factor for the water path length is calculated for each tube voltage shown as the waveform 80—left vertical scale. The noise for the water path length is calculated at the maximum tube power, as shown as the waveform 82—see right vertical scale. If the noise is higher than a noise baseline ($N_0$), i.e. $N>N_0$, it means that the corresponding tube voltage is not applicable since even the maximum tube power cannot achieve sufficient image quality. The noise baseline ($N_0$) may be set according to particular applications. The optimal tube voltage (Opt. kV) is the tube voltage corresponding to the maximum Q-factor with the tube power constraint. Thus, the optimal tube voltage can be written as the expression (1):

$$\text{opt.kV}:=\{kV|\text{argmax}Q(kV), N(kV)<N_0\} \quad (1)$$

Figure 6:
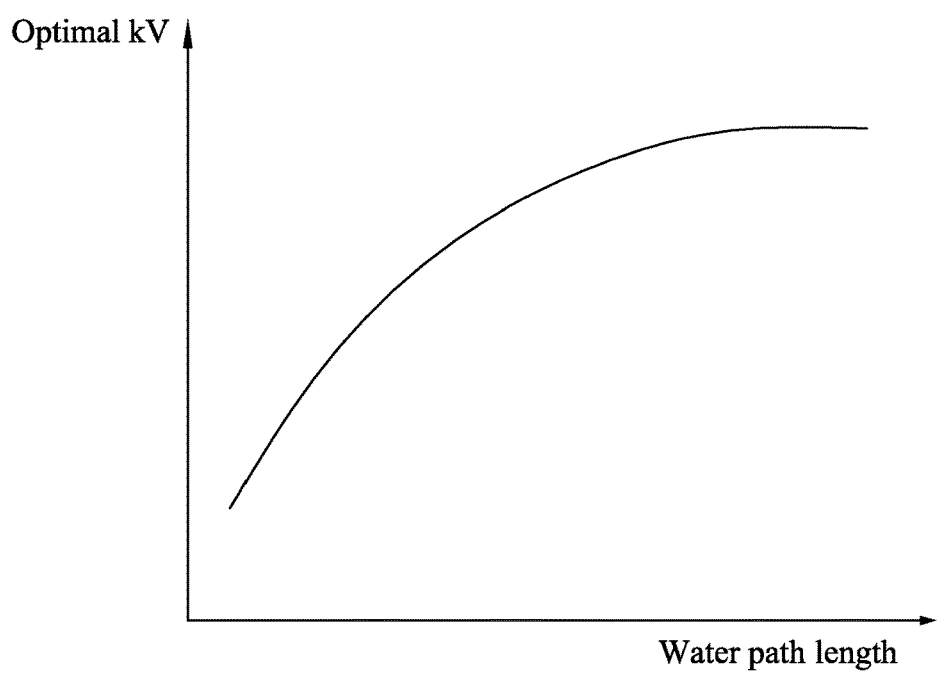
FIG. 6 is a waveform diagram of a relationship between optimal tube voltage and water path length according to one embodiment.

The waveforms of the Q-factor and the noise are generated for each water path length, and the optimal tube voltage is calculated for each water path length. Accordingly, the lookup table 76 is generated; a plot of representative data is shown in FIG. 6, which illustrates the relationship between the optimal tube voltage (Opt. kV) and the water path length. In one embodiment, the lookup table 76 may be generated offline.

Figure 7:
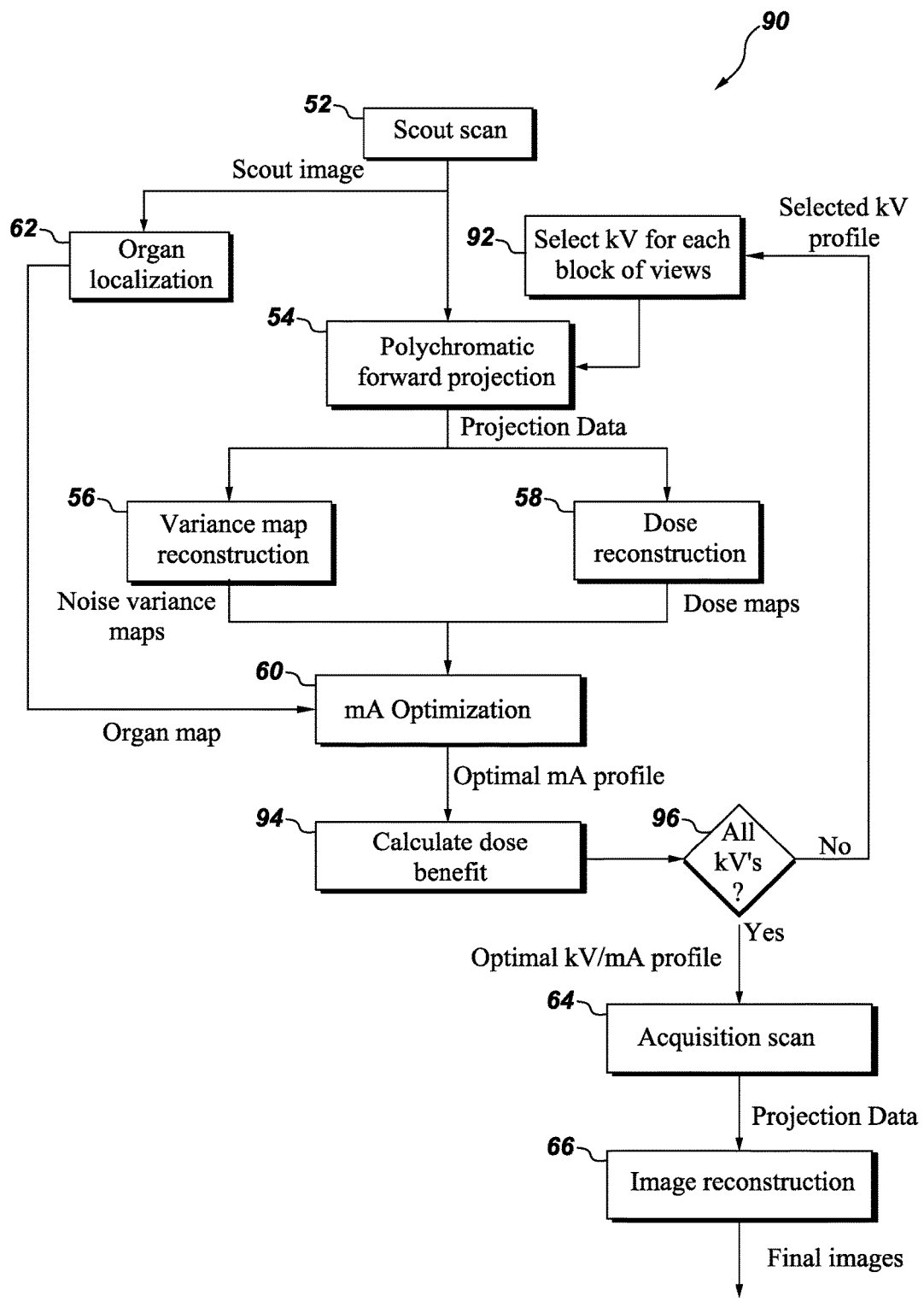
FIG. 7 is a flow chart of the imaging method according to another embodiment.
Figure 8:
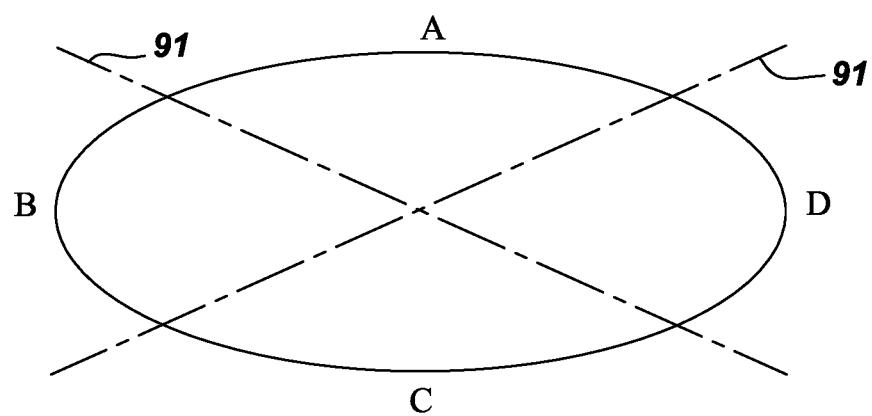
FIG. 8 is a schematic view of blocks of views according to one embodiment.

FIG. 7 illustrates a flow chart of a CT imaging method 90 according to another embodiment. The imaging method 90 in FIG. 7 is similar to the imaging method 50 in FIG. 3. In the embodiment of FIG. 7, all of the projection data are divided into two or more than two blocks of projection data (views). With reference to FIG. 8, in this embodiment, the views are divided into four blocks A, B, C and D along lines 91. It should be noted that this example is merely illustrative and is non-limiting.

The method 90 includes selecting a constant value from a voltage value group as the tube voltage for each block of views in block 92. The voltage value group includes voltage values applicable for the x-ray source. In one embodiment, the voltage value group is a group of 80 kV, 100 kV, 120 kV and 140 kV. In another embodiment, the voltage value group is a group of 80 kV, 90 kV, 100 kV, 110 kV, 120 kV 130 kV and 140 kV. The voltage value group is not limited to the examples above, which may be set according to particular types of the x-ray sources. One constant value is selected for one or more block of views, and there are multiple permutations and combinations of the values in the voltage value group for the collective blocks of views. Each of the permutations and combinations refers to as a voltage profile herein.

The action in block 54 in FIG. 7 is similar to the action in block 54 in FIG. 3. The projection data are generated based on the selected voltage values and constant tube current through forward projection of the scout image using a polychromatic spectrum. The noise variance maps and the dose maps are further generated view by view using the constant tube current in the blocks 56 and 58. The tube current profile is optimized view by view based on the noise variance maps, the dose maps and the organ map or localization in the block 60 which is similar to the embodiment in FIG. 3.

In block 94, dose benefit is calculated based on the selected voltage profile and the optimal tube current profile. In block 96, the method 90 further includes judging whether all the voltage profiles are selected to calculate the dose benefit. If not all the voltage profiles are selected, the processes in the blocks 92, 54, 56, 58, 60, 94 are circularly programed until all the voltage profiles are selected to generate the optimal current profiles and calculate dose benefits for all the voltage profiles and the optimal current profiles. The optimal current profile and the selected voltage profile with highest dose benefits are selected as the optimal voltage/current profile for the acquisition scan. Thereby, the radiation dose is minimized while maintaining the image quality based on the tube voltage and the tube current profiles, and the optimal tube voltage and the optimal tube current profiles are those that produce the required image quality using the lowest dose.

The actions in blocks 64 and 66 in FIG. 7 are similar to the actions in the blocks 64 and 66 in FIG. 3. The tube voltages and the tube currents are applied by the x-ray source based on the optimal voltage/current profile to scan the object and the final image is reconstructed based on the projection data from the acquisition scan. In the embodiment of FIG. 7, the tube voltages are selected and the tube current profile is modulated. The tube voltages and the tube current profile are optimized sequentially.

Figure 9:
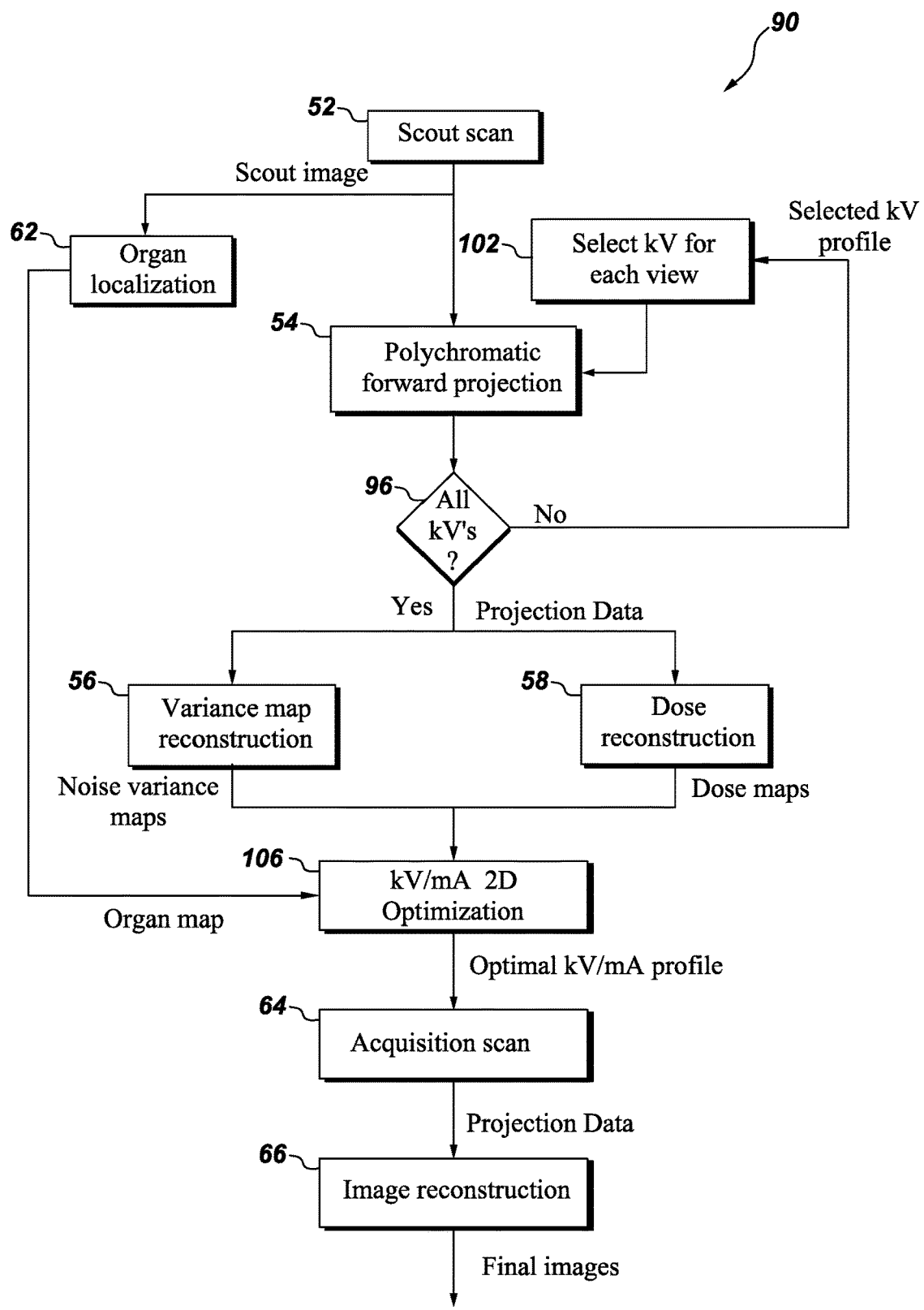
FIG. 9 is a flow chart of the imaging method according to another embodiment.

FIG. 9 illustrates a flow chart of a CT imaging method 100 according to another embodiment. The method 100 in FIG. 9 is similar to the method 90 in FIG. 7. Compared with the method 90 in FIG. 7, in the embodiment of FIG. 9, the method 100 includes selecting a constant value from the voltage value group as the tube voltage for each view in block 102. The projection data for each view are generated based on the selected voltage and the scout image for a constant current. The projection data may be stored in a memory.

In block 104, the method 100 includes judging whether all the voltage values have been selected for each view to generate the projection data. The projection data are generated for all the voltage values for each view. In block 56, the noise variance maps are generated for all the voltage values for a constant current and for all the views. In block 58, the dose maps are also generated for all the voltage values for a constant current and for all the views. In block 106, the tube voltage and the tube current profiles are optimized jointly according to the noise variance maps and the dose maps. In this embodiment, the tube voltage and the tube current profiles are also optimized based on the organ map or localization from the block 62. For each view, the tube voltage and the tube current are optimized to get optimal tube voltage and optimal tube current values. For all views, corresponding optimal tube voltage and optimal tube current are obtained so that an optimal voltage/current profile is obtained.

The actions in blocks 64 and 66 in FIG. 9 are similar to the actions in the blocks 64 and 66 in FIGS. 3 and 7. The tube voltage and the tube current profiles are applied by the x-ray source based on the optimal voltage/current profile to scan the object and the final image is reconstructed based on the projection data from the acquisition scan. In the embodiment of FIG. 9, the tube voltages are selected and the tube current is modulated, and the tube voltages and the tube current profile are optimized jointly. In another embodiment, the tube voltage may be modulated in block 102 and the tube voltage and the tube current profiles jointly optimized jointly.

In some embodiments, the tube hardware capability adds an extra constraint to the tube voltage/tube current relationship. For an x-ray tube containing a filament, there is a fixed relationship between tube voltage and tube current at each filament temperature, and there is a maximum speed for filament temperature change. The modulation of tube current is constrained by the modulation of tube voltage. Therefore the optimization engine can generate the optimal profile for both tube voltage and tube current simultaneously.

In some embodiments, the tube current profile may be optimized through selecting a constant value from a current value group. The current values of the current value group are applicable for the type of x-ray source. One current value may be selected for one view or for a block of views. In some embodiments, the tube currents may be optimized first and then the tube voltages optimized based on the optimal currents.

In some embodiments, a contrast agent, such as iodine, is administered orally or injected intravenously for a contrast-enhanced scan. The contrast agent is added to the contrast-enhanced organs, such as heart, that are identified in the organ map of the patient based on the first image. In exams that use a contrast agent, the image contrast in regions where this agent is present may be a critical parameter in defining image quality. For some contrast agents, like those that employ iodine, image quality may improve using lower x-ray energies, whereas if another contrast-enhancing element were used, there may be a different relationship between image quality and x-ray energy. It will be appreciated by those skilled in the art that the present invention is applicable to optimize the current and voltage profiles based on the presence of any x-ray contrast agent or any plurality of agents employed simultaneously, including but not limited to contrast agents that employ barium, iodine, gadolinium, bismuth, or other elements with atomic numbers in the range of these, as x-ray attenuating elements, whether these contrast agents are administered orally, intravenously, subcutaneously, or by some other means.

The contrast agent dose is the amount of the contrast agent injected into the patient. In some embodiments (e.g. patients with compromised renal function, but who are perhaps less sensitive to radiation dose), the tube voltage and the tube current may be optimized to permit minimizing the contrast agent dose while maintaining the image quality and perhaps allowing an increase in the radiation dose. The optimal tube voltage and the optimal tube current profiles are the tube voltages and the tube currents that permit administration of the lowest contrast agent dose.

In some embodiments (e.g. young patients with healthy renal systems, but who are perhaps more sensitive to radiation dose), the tube voltage and the tube current may be optimized to permit minimizing the radiation dose while maintaining the image quality and perhaps allowing an increase in the contrast agent dose. The optimal tube voltage and the optimal tube current profiles are the tube voltages and the tube currents that permit minimizing the radiation dose.

While the actions of the methods 50, 53, 90 and 100 are illustrated as functional blocks, the order of the blocks and the separation of the actions among the various blocks shown in FIGS. 3, 4, 7 and 9 are not intended to be limiting. For example, the blocks may be performed in a different order and an action associated with one block may be combined with one or more other blocks or may be subdivided into a number of blocks.

An imaging system like the CT imaging system 10 in FIGS. 1 and 2 is disclosed in the present disclosure to implement the imaging methods 50, 53, 90 and 100. The imaging system includes a controller, for example, including the controllers 28, 30, 44, the DAS 32, the computer 36 and the image reconstructor 34 in FIG. 2. The controller is configured to control the x-ray source and the detectors to execute the low-dose preparatory scan to the object, generate the first image, optimize the voltage profile and the current profile, control executing the acquisition scan and generate the second image. The details of the system and the operation process of the system are described above in FIGS. 1-9, which are not described again.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method, comprising:
    executing a low-dose preparatory scan to an object by applying tube voltages and tube currents in an x-ray source;
    generating a first image of the object corresponding to the low-dose preparatory scan;
    generating at least one of a plurality of image quality estimates and at least one of a plurality of dose estimates view by view at least based on the first image;
    optimizing the tube voltages and the tube currents to generate optimal profiles for the tube voltage and the tube current, at least one of the optimal profiles for the tube voltage and the tube current being generated based on at least one of the plurality of image quality estimates and at least one of the plurality of dose estimates, wherein optimizing the tube voltages and the tube currents comprises selecting a constant value from a corresponding value group as the tube voltage or the tube current for one or more views, modulating the tube voltages or the tube currents view by view, or a combination thereof;

executing an acquisition scan by applying the tube voltages and the tube currents based on the optimal profiles; and generating a second image of the object corresponding to the acquisition scan.

2. The method of claim 1, wherein optimizing the tube voltages and the tube currents comprises optimizing the tube voltages and the tube currents sequentially.

3. The method of claim 1, wherein optimizing the tube voltages and the tube currents comprises optimizing the tube voltages and the tube currents jointly.

4. The method of claim 1, wherein optimizing the tube voltages and the tube currents comprises optimizing the tube voltages based on the first image generated from an acquisition using a constant tube current to get the optimal profile for the tube voltages.

5. The method of claim 4, wherein at least one of the plurality of image quality estimates and at least one of the plurality of dose estimates are generated based on the optimal profile for the tube voltages.

6. The method of claim 1, wherein the tube currents are optimized at least in part based on at least one of the plurality of image quality estimates and at least one of the plurality of dose estimates.

7. The method of claim 1, further comprising generating an organ map of the object based on the first image, wherein at least one of the optimal profiles for the tube voltage and the tube current is generated based on the organ map.

8. The method of claim 1, wherein optimizing the tube voltages and the tube currents comprises selecting a constant value from a voltage value group as the tube voltage for one or more views.

9. The method of claim 1, wherein optimizing the tube voltages and the tube currents comprises selecting a constant value from a current value group as the tube current for one or more views.

10. The method of claim 1, wherein optimizing the tube voltages and the tube currents comprises modulating the tube voltages view by view by continuously changing the tube voltage as a gantry rotates about the object.

11. The method of claim 1, wherein optimizing the tube voltage and the tube currents comprises modulating the tube currents view by view by continuously changing the tube current as a gantry rotates about the object.

12. The method of claim 1, further comprising calculating dose benefits based on the tube voltages and the tube currents, and selecting the tube voltages and the tube currents with the highest dose reduction benefits to generate the optimal profiles.

13. An imaging system, comprising:
a plurality of detectors;
an x-ray source configured to project x-rays towards the plurality of detectors;
a controller operatively connected to the x-ray source and the plurality of detectors and configured to:
control the x-ray source and the plurality of detectors to execute a low-dose preparatory scan to an object by applying tube voltages and tube currents in the x-ray source;
generate a first image of the object corresponding to the low-dose preparatory scan;
generate at least one of a plurality of image quality estimates and at least one of a plurality of dose estimates view by view at least based on the first image;
optimize the tube voltages and the tube currents to generate optimal profiles for the tube voltage and the tube current, at least one of the optimal profiles for the tube voltage and the tube current being generated based on at least one of the plurality of image quality estimates and at least one of the plurality of dose estimates, wherein optimizing, the tube voltages and the tube currents comprises selecting a constant value from a corresponding value group as the tube voltage or the tube current for one or more views, modulating the tube voltages or the tube currents view by view, or a combination thereof;
apply in the x-ray source the tube voltages and the tube currents based on the optimal profiles to execute an acquisition scan; and
generate a second image of the object corresponding to the acquisition scan.

14. The imaging system of claim 13, wherein the controller is configured to optimize the tube voltages and the tube currents sequentially.

15. The imaging system of claim 13, wherein the controller is configured to optimize the tube voltages and the tube currents jointly.

16. The imaging system of claim 13, wherein the controller is configured to optimize the tube voltages based on the first image from an acquisition using a constant tube current to generate the optimal profile for the tube voltage.

17. The imaging system of claim 13, wherein the controller is configured to select a constant value from a voltage value group as the tube voltage for one or more views.

18. The imaging system of claim 13, wherein the controller is configured to select a constant value from a current value group as the tube current for one or more views.

19. The imaging system of claim 13, wherein the controller is configured to modulate the tube voltages view by view by continuously changing the tube voltage as a gantry rotates about the object.

20. The imaging system of claim 13, wherein the controller is configured to modulate the tube currents view by view by continuously changing the tube current as a gantry rotates about the object.

* * * * *